United States Patent [19]

King

[11] Patent Number: 4,853,376
[45] Date of Patent: Aug. 1, 1989

[54] BENZAMIDES AND BENZOATES HAVING ANTI-EMETIC ACTIVITY

[75] Inventor: Francis D. King, Harlow, England

[73] Assignee: Beecham Group, p.l.c., Brentford, England

[21] Appl. No.: 920,022

[22] Filed: Oct. 17, 1986

[30] Foreign Application Priority Data

Oct. 19, 1985 [GB] United Kingdom ............. 8525844

[51] Int. Cl.$^4$ .................. A61K 31/62; A61K 31/435; C07D 453/02
[52] U.S. Cl. ................................. 514/161; 514/305; 546/133
[58] Field of Search ............. 546/133, 137; 514/305, 514/161

[56] References Cited

U.S. PATENT DOCUMENTS

| | | | |
|---|---|---|---|
| 3,405,134 | 10/1968 | Judd | 546/133 |
| 3,725,419 | 3/1973 | Judd et al. | 546/133 |
| 4,213,983 | 7/1980 | Hadley et al. | 546/133 |
| 4,612,319 | 9/1988 | King | 514/305 |
| 4,721,720 | 1/1988 | Wootton et al. | 514/304 |

FOREIGN PATENT DOCUMENTS

| | | | |
|---|---|---|---|
| 0099789 | 2/1984 | European Pat. Off. | 546/133 |
| 0158532 | 10/1985 | European Pat. Off. | 546/133 |
| 0229444 | 7/1987 | European Pat. Off. | 546/133 |
| 2100940 | 3/1972 | France | 546/133 |
| 1293446 | 10/1972 | United Kingdom | 546/133 |
| 2125398 | 6/1983 | United Kingdom | 546/133 |
| 84/00166 | 1/1984 | World Int. Prop. O. | 546/133 |

OTHER PUBLICATIONS

Biniecki, CA 94:15530n (1981).
Biniecki, CA 98:197986d (1983).
Physicians' Desk Reference (1988) pp. 1696-1698.
Chem. Abstracts, vol. 100 (No. 25) abst No. 100:209,629q, Jun. 18, 1984.
Chem. Abstracts, vol. 69 (No. 9) abst. No. 69:35886v, Aug. 26, 1968.
Noller, Textbook of Organic Chemistry, 3rd Edition, 1966, W. B. Saunders Co., Philadelphia, p. 226.

*Primary Examiner*—Richard A. Schwartz
*Assistant Examiner*—Robert C. Whittenbaugh
*Attorney, Agent, or Firm*—James F. Haley, Jr.; David K. Barr

[57] ABSTRACT

Compounds of formula (I) and pharmaceutically acceptable salts thereof:

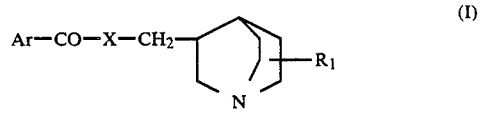

(I)

wherein:
X is NH; or O when Ar is of formula (a) and $R_2$ is hydrogen or when Ar is a group of formula (b);
$R_1$ is hydrogen, $C_{1-6}$ alkyl, phenyl or phenyl-$C_{1-6}$ alkyl, which phenyl moieties may be substituted by $C_{1-6}$ alkyl, $C_{1-6}$ alkoxy or halogen;
Ar is a group of formula (a):

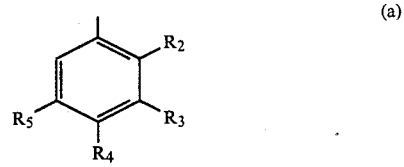

(a)

wherein $R_2$, $R_3$, $R_4$ and $R_5$ are optional substituents; or Ar is a group of formula (b):

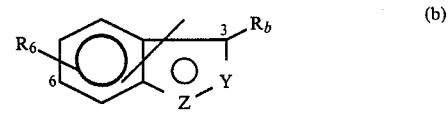

(b)

wherein
Z is $CH_2$, O, S or $NR_7$ wherein $R_7$ is hydrogen, $C_{1-6}$ alkyl, $C_{3-7}$ alkenyl-methyl, phenyl or phenyl $C_{1-4}$ alkyl either of which phenyl moieties may be substituted by one or two of halogen, $CF_3$, $C_{1-6}$ alkoxy or $C_{1-6}$ alkyl; and Y is CH or N; or Z is CH or N and Y is $NR_a$ or $CHR_a$ where $R_a$ is as defined for $R_7$ above;
$R_b$ is present when the COX linkage is attached at the phenyl ring, and is selected from hydrogen, halogen, $CF_3$, hydroxy, $C_{1-6}$ alkoxy or $C_{1-6}$ alkyl;
$R_6$ is an optional substituent having anti-emetic activity and may also have gastric motility enhancing activity, and/or 5-HT M-receptor antagonist activity, a process for their preparation and their use as pharmaceuticals.

12 Claims, No Drawings

BENZAMIDES AND BENZOATES HAVING ANTI-EMETIC ACTIVITY

This invention relates to substituted benzamides and benzoates having pharmacological activity, to a process for their preparation and to their use as pharmaceuticals.

EP-A-No. 99789 discloses a group of benzamides having a 3-quinuclidinyl side chain and having gastric motility enhancing activity. UK Pat. No. 2,125,398 discloses a group of benzamides and benzoates having a quinuclidinyl side chain and having serotonin M antagonist activity.

A structurally distinct group of compounds has now been discovered which compounds have gastric motility enhancing and/or anti-emetic activity and/or 5-HT M-receptor antagonist activity.

Accordingly, the present invention provides a compound of formula (I) or a pharmaceutically acceptable salt thereof:

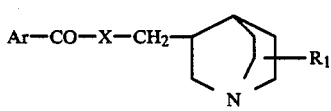

wherein:
X is NH; or O when Ar is of formula (a) and $R_2$ is hydrogen or when Ar is a group of formula (b);
$R_1$ is hydrogen, $C_{1-6}$ alkyl, phenyl or phenyl-$CZ_{1-6}$ alkyl, which phenyl moieties may be substituted by $C_{1-6}$ alkyl, $C_{1-6}$ alkoxy or halogen;
Ar is a group of formula (a):

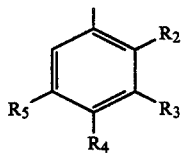

wherein either $R_2$ is $C_{1-6}$ alkoxy and one of $R_3$, $R_4$ and $R_5$ is hydrogen and the other two are selected from hydrogen, halogen, $CF_3$, $C_{1-6}$ alkoxy, $C_{1-6}$ alkyl, $C_{1-6}$-alkylthio, $C_{2-5}$ alkanoyl, $C_{1-10}$ carboxylic acylamino, $C_{1-6}$-alkyl S(O)n wherein n is 0, 1 or 2, nitro or amino, aminocarbonyl or aminosulphonyl optionally substituted by one or two groups selected from $C_{1-6}$ alkyl, $C_{3-8}$ cycloalkyl, $C_{3-8}$ cycloalkyl $C_{1-4}$ alkyl or phenyl $C_{1-4}$ alkyl groups any of which phenyl moieties may be substituted by one or two groups selected from halogen, $CF_3$, $C_{1-6}$ alkyl or $C_{1-6}$ alkoxy; or $R_2$ is hydrogen and $R_3$, $R_4$ and $R_5$ are independently selected from hydrogen, $C_{1-6}$ alkyl, hydroxy, $C_{1-6}$ alkoxy, $C_{1-6}$ alkylthio or halo; or any two on adjacent carbon atoms together are $C_{1-2}$ alkylenedioxy and the third is hydrogen, $C_{1-6}$ alkyl, $C_{1-6}$ alkoxy or halo;
or Ar is a group of formula (b):

wherein
Z is $CH_2$, O, S or $NR_7$ wherein $R_7$ is hydrogen, $C_{1-6}$ alkyl, $C_{3-7}$ alkenyl-methyl, phenyl or phenyl $C_{1-4}$ alkyl either of which phenyl moieties may be substituted by one or two of halogen, $CF_3$, $C_{1-6}$ alkoxy or $C_{1-6}$ alkyl; and Y is CH or N; or Z is CH or N and Y is $NR_a$ or $CHR_a$ where $R_a$ is as defined for $R_7$ above;
$R_b$ present when the COX linkage is attached at the phenyl ring, and is selected from hydrogen, halogen, $CF_3$, hydroxy, $C_{1-6}$ alkoxy or $C_{1-6}$ alkyl;
$R_6$ is hydrogen, halogen, $CF_3$, $C_{1-6}$ alkyl, $C_{1-6}$ alkoxy, $C_{1-6}$ alkylthio, $C_{1-7}$ acyl, $C_{1-7}$ acylamino, $C_{1-6}$ alkylsulphonylamino, N-($C_{1-6}$ alkylsulphonyl)-N-$C_{1-4}$ alkylamino, $C_{1-6}$ alkylsulphinyl, hydroxy, nitro or amino, aminocarbonyl, aminosulphonyl, aminosulphonylamino or N-(aminosulphonyl)-$C_{1-4}$ alkylamino optionally N-substituted by one or two groups selected from $C_{1-6}$ alkyl, $C_{3-8}$ cycloalkyl, $C_{3-8}$ cycloalkyl $C_{1-4}$ alkyl, phenyl or phenyl $C_{1-4}$ alkyl groups or optionally N-disubstituted by $C_{4-5}$ polymethylene.

X is often NH.
Suitable examples of $R_1$, include hydrogen, methyl, ethyl, n- and iso-propyl, n, sec- and tert-butyl; phenyl, phenylmethyl and phenylethyl, which phenyl moieties may be substituted by one or two methyl, ethyl, n- and iso-propyl, n-, sec- and tertbutyl; methoxy, ethoxy and n- and iso-propoxy; $CF_3$, fluoro, chloro or bromo.
Preferably $R_1$ is hydrogen
When Ar is a group of formula (a), examples of $R_2$ when $C_{1-6}$ alkoxy include methoxy, ethoxy and n- and iso-propoxy. Preferably $R_2$ is a methoxy group.
Suitable examples of $R_3$, $R_4$ and $R_5$ then include the following atoms and groups: hydrogen; chloro, bromo, $CF_3$, methylthio, ethylthio, n and iso-propylthio; formyl, acetyl, propionyl, n- and iso-butyryl; formylamino, acetylamino, propionylamino, n- and iso-butyrylamino; methyl, ethyl and n- and iso-propylsulphone, -sulphinyl, -thia; nitro; methoxy, ethoxy and n- and iso-propoxy; hydroxy; amino, aminosulphonyl substituted by one or two methyl, ethyl, n- or iso-propyl groups, or by $C_2$, $C_4$ or $C_5$ cycloalkyl or by benzyl optionally substituted as defined above. Particularly suitable $R_4$ and $R_5$ groups include hydrogen, halogen, and amino; and as "intermediates", acylamino and nitro, which can conveniently be converted to the corresponding amino groups.
Particularly preferred $R_4$ groups include 4-amino and 4-acylamino, Most preferably $R_4$ is 4-amino. Particularly preferred $R_5$ groups include 5-halo, such as 5-chloro.
In another group of compounds $R_4$ is hydrogen, 4-halo (eg chloro), or amino; and $R_5$ is 5-$C_{1-6}$ alkyl S (O)n (such as 5-methylsulphonyl, -sulphinyl or -thio) or 5-optionally alkylated aminosulphonyl.
When $R_2$ is hydrogen, examples of $R_3$ include halo, such as chloro, $C_{1-6}$ alkoxy, such as methoxy and $C_{1-6}$ alkyl, such as methyl. Preferably $R_3$ is chloro or methyl.
Examples of $R_4$ then include hydrogen, halo, such as chloro, hydroxy and $C_{1-6}$ alkoxy such as methoxy. Preferably $R_4$ is hydrogen or chloro.
Examples of $R_5$ then include hydrogen, halo such as chloro and $C_{1-6}$ alkoxy, such as methoxy and $C_{1-6}$ alkyl, such as methyl. Preferably $R_5$ is hydrogen, chloro or methyl.
Z is often $NR_7$ and Y is CH or N; or Z is N and $R_a$ is as defined for $R_7$.

Suitable values for $R_7$ or $R_a$ include hydrogen, methyl, ethyl, n- and iso-propyl; prop-2-enyl, but-2-enyl, but-3-enyl, 1-methylenepropyl and 1-methylprop-2-yl in their E and Z forms where stereoisomerism exists, phenyl and benzyl optionally substituted by one or two of chloro, bromo, $CF_3$, methoxy, ethoxy, n-and iso-propoxy, methyl, ethyl, n- and iso-propyl. Often $R_7/R_a$ is hydrogen, methyl or ethyl.

Suitable values for $R_b$ when present include hydrogen, chloro, bromo, $CF_3$, methoxy, ethoxy, n- and iso-propoxy, methyl, ethyl, n- and iso-propyl.

Often the —COX— linkage is attached at positions 3 or 6, as depicted in formula (b).

Values for $R_6$ include hydrogen, fluoro, chloro, bromo, $CF_3$, methyl, ethyl, methoxy, ethoxy, methylthio, ethylthio, acetyl, prionyl, acetylamino, methylsulphonylamino, methylsulphinyl, hydroxy, nitro; and amino, aminocarbonyl, aminosulphonyl, aminosulphonylamino or N-(aminosulphonyl)-methylamino any of which may be optionally substituted by one or two methyl groups or by a cyclopentyl or cyclohexyl group of distributed by $C_4$ or $C_5$ polymethylene; $R_6$ is often hydrogen or 5-fluoro.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

The pharmaceutically acceptable salts of the compounds of the formula (I) are usually acid addition salts with acids such as hydrochloric, hydrobromic, phosphoric, sulphuric, citric, tartaric, lactic and acetic acid.

Preferably the acid addition salt is the hydrochloride salt.

Examples of pharmaceutically acceptable salts include quaternary derivatives of the compounds of formula (I) such as the compounds quaternised by compounds $R_8$-T wherein $R_8$ is $C_{1-6}$ alkyl, phenyl-$C_{1-6}$ alkyl or $C_{5-7}$ cycloalkyl, and T is a radical corresponding to an anion of an acid. Suitable examples of $R_8$ include methyl, ethyl and n- and iso-propyl; and benzyl and phenethyl. Suitable examples of T include halide such as chloride, bromide and iodide.

The compounds of formula (I) may also form internal salts such as pharmaceutically acceptable N-oxides.

The compounds of the formula (I), their pharmaceutically acceptable salts, (including quaternary derivatives and N-oxides) may also form pharmaceutically acceptable solvates, such as hydrates and these are included wherever a compound of formula (I) and salts thereof are herein referred to.

It will of course be realised that some of the compounds of the formula (I) have chiral or prochiral centres and thus are capable of existing in a number of stereoisomeric forms including enantiomers. The invention extends to each of these stereoisomeric forms (including enantiomers), and to mixtures thereof (including racemates). The different stereoisomeric forms may be separated one from the other by the usual methods.

It will also be realised that compounds of the formula (I) wherein $R_7$ is hydrogen can exist as two tautomeric forms i.e. that wherein $R_7$ is hydrogen and Y is CH or N and that wherein $R_a$ is hydrogen and Z is N. The invention extends to each of these forms and to mixtures thereof. The predominant tautomeric form is usually that wherein $R_7$ is hydrogen.

A group of compounds within formula (I) is of formula (II):

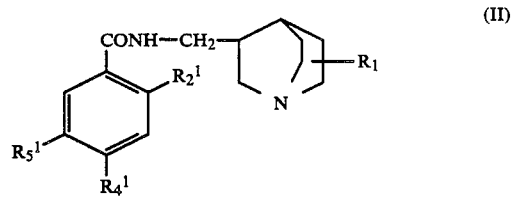

(II)

wherein
$R_2^1$ is $C_{1-6}$ alkoxy;
$R_4^1$ is amino or $C_{1-7}$ alkanoylamino;
$R_5^1$ is halo or $C_{1-6}$ alkylthio;
and the remaining variables are as defined in formula (I). Suitable examples and preferred values for the variables are as described for the corresponding variables under formula (I).

There is a further group of compounds within formula (I) of formula (III):

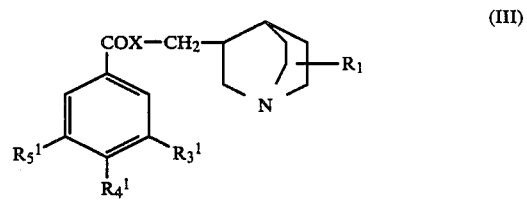

(III)

wherein
$R_3^1$ is halo, $C_{1-6}$ alkoxy or $C_{1-6}$ alkyl;
$R_4^2$ is hydrogen or $C_{1-6}$ alkoxy;
$R_5^2$ is halo, $C_{1-6}$ alkoxy or $C_{1-6}$ alkyl; and
the remaining variables are as defined in formula (I).

Suitable examples and preferred values for the variables are as described for the corresponding variables under formula (I).

There is another group of compounds within formula (I) of formula (IV):

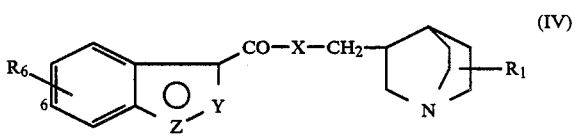

(IV)

wherein the variables are as defined in formula (I).

Suitable examples and preferred values for the variables are as described for the corresponding variables under formula (I).

The invention also provides a process for the preparation of a compound of formula (I) which process comprises reacting a compound of formula (V):

Ar G  (V)

with a compound of formula (VI):

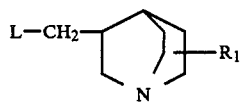

(VI)

wherein

G is COQ where Q is a leaving group and L is NH$_2$ or OH or a reactive derivative thereof and the remaining variables area as hereinbefore defined; and thereafter optionally converting any R$_2$, R$_3$, R$_4$, R$_5$, R$_6$, R$_2$ and R$_b$ group to another R$_2$, R$_3$, R$_4$, R$_5$, R$_a$ and R$_b$ group respectively, and optionally forming a pharmaceutically acceptable salt of the resultant compound of formula (I).

Examples of leaving groups Q, displaceable by a nucleophile, include halogen such as chloro and bromo, hydroxy, carboxylic acyloxy such as C$_{1-4}$ alkanoyloxy or C$_{1-4}$ alkoxycarbonyloxy and activated hydrocarbyloxy such as pentachlorophenoxy.

Alternatively, when G is COQ, Ar is of formula (b) and Z is NH in formula (V), a nitrogen heterocycle may act as the leaving group i.e. that obtained by reaction of a compound of formula (V) wherein G is CO$_2$H with thionyl chloride to give a diindazolo[2,3, a,2', 3'-d]-pyrazine-7,14-dione.

If a group Q is a halide, then the reaction is preferably carried out at non-extreme temperatures in an inert non-hydroxylic solvent, such as benzene, dichloromethane, toluene, diethyl ether, tetrahydrofuran (TF) or dimethylformamide (DMF). It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate. Temperatures of 0°–100° C., in particular 10°–80° C. are suitable.

If a group Q is hydroxy, then the reaction is generally carried out in an inert non-hydroxylic solvent, such as dichloromethane, THF or DMF optionally in the presence of a dehydrating agent such as a carbodiimide, for example dicyclohexylcarbodiimide. The reaction may be carried out at any non-extreme temperature, such as -10 to 100° C., for example, 0 to 80° C. Generally, higher reaction temperatures are employed with less active compounds whereas lower temperatures are employed with the more active compounds.

If a group Q is carboxylic acyloxy, then the reaction is preferably carried in substantially the same manner as the reaction when Q is halide. Suitable examples of acyloxy leaving groups included C$_{1-4}$ alkanoyloxy and C$_{1-4}$ alkoxycarbonyloxy, in which case the reaction is preferably carried out in an inert solvent, such as dichloromethane, at a non-extreme temperature for example ambient temperatures in the presence of an acid acceptor, such as triethylamine. C$_{1-4}$ alkoxycarbonyloxy leaving groups may be generated in situ by treatment of the corresponding compound wherein Q is hydroxy with a C$_{1-4}$ alkyl chloroformate.

If a group Q is activated hydrocarbyloxy then the reaction is preferably carried out in an inert polar solvent, such as dimethylformamide. It is also preferred that the activated hydrocarbyloxy group is a pentachlorophenyl ester and that the reaction is carried out at ambient temperature.

When the leaving group Q is a nitrogen heterocycle as hereinbefore described the reaction is carried out in a similar manner as when Q is a halide.

When L is OH or a reactive derivative thereof, the reactive derivative is often a salt, such as the lithium salt.

Pharmaceutically acceptable salts of the compounds of this invention may be formed conventionally.

The salts may be formed for example by reaction of the base compound of formula (I) with a pharmaceutically acceptable organic or inorganic acid.

It will be apparent that compounds of the formula (I) containing an R$_2$, R$_3$, R$_4$, R$_5$, R$_6$, R$_a$ or R$_b$ group which is convertible to another R$_2$, R$_3$, R$_4$, R$_5$, R$_6$, R$_a$ or R$_b$ group are useful novel intermediates. A number of such conversions is possible not only for the end compounds of formula (I), but also for their intermediates as follows:

(i) a hydrogen substituent is convertible to a nitro substituent by nitration;

(ii) a nitro substituent is convertible to an amino substituent by reduction;

(iii) a C$_{1-7}$ acylamino substituent is convertible to an amino substituent by deacylation;

(iv) an amino substituent is convertible to a C$_{1-4}$ acylamino substituent by acylation with a carboxylic acid derivative;

(v) a hydrogen substituent is convertible to a halogen substituent by halogenation;

(vi) a C$_{1-6}$ alkylthio or C$_{1-6}$ alkylsulphinyl substituent is convertible to a C$_{1-6}$ alkylsulphinyl or a C$_{1-6}$ alkysulphonyl substituent respectively by oxidation;

(vii) an amino, aminocarbonyl, aminosulphonyl, aminosulphonylamino or N-(aminosulphonyl)-N-C$_{1-4}$ alkylamino substituent is convertible to a corresponding substituent substituted by one or two groups selected from C$_{106}$ alkyl, C$_{3-8}$ cycloalkyl, C$_{104}$ alkyl or phenyl C$_{1-4}$ alkyl groups any of which phenyl groups may be substituted by one or more groups selected from halogen, trifluoromethyl, C$_{1-6}$ alkyl, C$_{1-6}$ alkoxy and nitro, or disubstituted by C$_{4-5}$ polymethylene , by N-alkylation;

(viii) an amino substituent is convertible to a C$_{1-6}$ alkylsulphonylamino group or an aminosulphonylamino group optionally N-substituted as defined by acylation with a C$_{1-6}$ alkylsulphonyl chloride or di-substituted aminosulphonyl chloride.

(ix) A C$_{1-4}$ alkylamino substituent group is convertible to a N-(C$_{1-6}$ alkylsulphonyl)N-C$_{1-4}$ alkylamino group or an N-(amino sulphonyl)N-C$_{1-4}$ alkylamino group optionally N-substituted as defined by acylation with a C$_{1-6}$ alkylsulphonyl chloride or di-substituted aminosulphonyl chloride.

Conversions (i) to (ix) are only exemplary and are not exhaustive of the possibilities.

In regard to (i), nitration is carried out in accordance with known procedures.

In regard to (ii), the reduction is carried out with a reagent suitable for reducing nitroanisole to aminoanisole.

In regard to (iii), deacylation is carried out by treatment with a base, such as an alkali metal hydroxide.

In regard to (iv), (viii), and (ix) the acylation is carried out with an acylating agent, such as the corresponding acid or acid chloride. Formylation is carried out with the free acid.

In regard to (v), halogenation is carried out with conventional halogenating agents.

In regard to (vi), oxidation is carried out at below ambient temperatures in a non-aqueous solvent, such as a chlorinated hydrocarbon, in the presence of an organic peracid, such as 3-chloroperbenzoic acid, or in water in the presence of a soluble strong inorganic oxidant, such as an alkali metal permanganate or in aqueous hydrogen peroxide. It will be realised that this process may also N-oxidise the N-moiety in the side chain and suitable precautions will routinely be taken by the skilled man.

In regard to (vii), alkylation is carried out with a corresponding alkylating agent such as the chloride or bromide under conventional conditions.

Before carrying out any of these conversions, the effect, if any, on other substituents should be considered, and such reagents as are appropriate should be selected together with the adoption of such precautionary measures as are necessary. For example, O-alkylation and O-acylation may also produce N-alkylated and N-acylated products respectively unless the nitrogen atom(s) is (are) previously protected. This may be conveniently achieved by carrying out the alkylation or acylation reaction in a strong acid, such as trifluoroacetic acid, which protonates, and thereby protects, the nitrogen atom(s).

The compounds of formula (V) and (VI) wherein L is OH are known or are preparable analogously to, or routinely from, known compounds.

Compounds of formula (VI) wherein L is $NH_2$ form an aspect of the present invention.

Compounds of formula (VI) wherein L is $NH_2$ may be prepared from the corresponding cyano compound by reduction with a hydride reducing agent, such as $LiAlH_4$; or from the corresponding L is OH compound by conversion to an activated form such as the mesylate or chloro derivative, then nucleophilic displacement with ammonia.

The compounds of the present invention have anti-emetic activity and may also have gastric motility enhancing and/or 5-HT antagonist activity, i.e. all the compounds have anti-emetic activity, but some also have other utilities. Compounds having gastric motility enhancing activity are useful in the treatment of disorders such as retarded gastric emptying, dyspepsia, flatulence, oesophageal reflux and peptic ulcer. Compounds having 5-HT antagonist activity are useful in the treatment of migraine, cluster headaches, trigeminal neuralgia and/or cytotoxic agent or radiation induced nausea and vomiting. Examples of cytotoxic agents include cisplatin, doxorubicin and cyclophosphamide. Compounds which are 5-HT antagonists may also be of potential use in the treatment of CNS disorders such as anxiety and psychosis; arrhythmia, obesity and irritable bowel syndrome.

Compounds of formula (I) of interest for their 5-HT antagonist activity are the compounds of formula (I) wherein Ar is of formula (a) and $R_2$ is hydrogen, or Ar is of formula (b). Compounds of formula (I) of interest for their gastric motility enhancing activity and anti-emetic activity are the compounds of formula (I) where Ar is of formula (a) and $R_2$ is $C_{1-6}$ alkoxy.

The invention also provides a pharmaceutical composition comprising a compound of formula (I), or a pharmaceutically acceptable salt thereof, and a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing.

Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of disorders relating to impaired gastrointestinal motility and/or emesis and/or migraine, cluster headaches, trigeminal neuralgia and/or radiation or cytotoxic agent induced nausea and vomiting in mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70kg adult will normally contain 0.5 to 1000mg for example 1 to 500mg, of the compound of the invention. Unit doses may be administered once or more than once a day, for example, 2, 3 or 4 times a day, more usually 1 to 3 times a day, that is in the range of approximatley 0.001 to 50 mg/kg/day, more usually 0.002 to 25 mg/kg/day.

No adverse toxicological effects were indicated at any of the aforementioned dosage ranges.

The invention also provides a compound of formula (I) or a pharmaceutically acceptable salt thereof for use as an active therapeutic substance, in particular for use in the treatment of disorders relating to impaired gastrointestinal motility and/or emesis and/or migraine, cluster headaches, trigeminal neuralgia and/or radiation or cytotoxic agent induced nausea and vomiting.

The following Examples illustrate the preparation of compounds of formula (I); the following Descriptions illustrate the preparation of intermediates.

DESCRIPTION 1

(±) 3-Aminomethyl quinuclidine (D1)

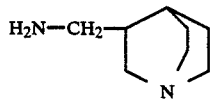

A solution of 3-cyanoquinuclidine (3.0g) was added to a stirred suspension of LiAlH$_4$ (1.1g) in dry THF (250ml) and the reaction heated to reflux for 3h. On cooling the reaction, water (1ml), 2.5N NaOH solution (1.5ml) and then water (2.5ml) were added carefully and the solids removed by filtration. Evaporation of the filtrate gave the title compound, D1 (3.1g) as an oil.

EXAMPLE 1

(±)
4-Acetamido-5-chloro-2-methoxy-N-(3-quinuclidinylmethyl)benzamide (E1)

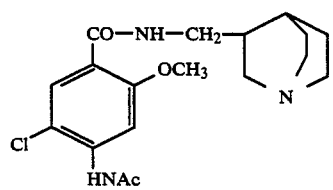

A stirred solution of 4-acetamido-5-chloro-2-methoxybenzoyl chloride (5.3g) in toluene (200ml) at 0° C. was treated with a solution of D1 (2.8g) and triethylamine (3ml) in toluene (50ml). The reaction mixture was stirred at room temperature for 3h, washed with 2.5N NaOH solution (20ml) and the aqueous layer re-extracted with EtOAC (100ml). The combined organic extracts were dried (K$_2$CO$_3$) and evaporated to dryness to give the title compound (E1) as an oil.

n.m.r. (δ, CDCl$_3$, 60 MHz),
8.29 (s, 1H),
8.18 (s, 1H),
8.10-7.50 (m, 2H),
3.98 (s, 3H),
3.70-3.25 (m, 2H),
3.20-1.20 (m, 15H including 2.26,. s, 3H).

EXAMPLE 2

(±)
4-Amino-5-chloro-2-methoxy-N-(3-quinuclidinylmethyl)benzamide (E2)

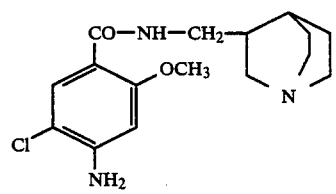

A solution of E1 (3g) and sodium hydroxide (0.6g) in ethanol (20ml) and water (5ml) was heated to reflux for 3h. The solvent was evaporated and the residue extracted into ethyl acetate. The organic extract was concentrated and purified by column chromatography (alumina, Brockman Grade II, CHCl$_3$) to give the title compound, E2 (1.2g)

mp 171°-3° C. (EtOAc/petrol)
n.m.r. (δ, CDCl$_3$, 79.5MHz),
8.10 (s, 1H),
7.80-7.50 (m, 1H),
6.30 (s, 1H),
3.88 (s, 3H),
3.44 (dd, 2H),
3.25-2.25 (m, 6H),
2.10-1.20 (m, 6H).

EXAMPLE 3

N-(3-Quinuclidinylmethyl)-1-methyl-indazole-3-carboxamide

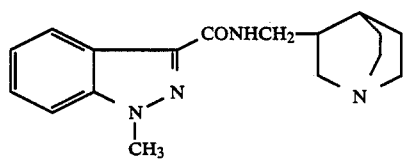

The title compound was prepared in a similar manner to that described in Example 1, by reacting the appropriate acid chloride with the compound of Description 1 (mp. 135°-6° C.)

PHARMACOLOGICAL DATA

1. Intragastric pressure in the rat

Intragastric pressure changes were recorded from fasted conscious and restrained rats using a saline filled catheter inserted into the lumen of the stomach via a permanent gastric fistula. The catheter was connected to a physiological pressure transducer and pressure changes recorded on a hot wire pen recorder. An index of activity was obtained by measuring the average height of pressure waves during 10 minute periods. Values for 4 such periods were obtained during assessment of spontaneous activity prior to dosing and for the 40 minute period following dosing with compound or vehicle. The Student's "t" test was applied to the means values obtained for activity prior to and post treatment. Groups of 10 animals were used for each treatment.

The compound of Example 2 was active at a dose of 0.25 mg/kg s.c.

2. Antagonism of the von Bezold-Jarisch reflex

The compounds were evaluated for antagonism of the von Bezold-Jarisch reflex evoked by 5-HT in the anaesthetised rat according to the following method:

Male rats 250–350 g, were anaesthetised with urethane (1.25 g/kg intraperitoneally) and blood pressure and hear rate recorded as described by Fozard J.R. et al., J. Cardiovasc. Pharmacol. 2, 229-245 (1980). A submaximal dose of 5-HT (usually 6 μg/kg) was given repeatedly by the intravenous route and changes in heart rate quantified. Compounds were given intravenously and the concentration required to reduce the 5-HT-evoked response to 50% of the control response ($ED_{50}$) was then determined.

The compound of Example 2 had an $ED_{50}$ value of 5.2±2.3 μg/kg.

I claim:

1. A compound of formula (I) or a pharmaceutically acceptable salt thereof:

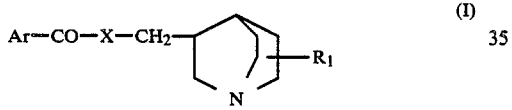

wherein:
X is HN; or O when Ar is of formula (a) and $R_2$ is hydrogen or when Ar is a group of formula (b);
$R_1$ is hydrogen, $C_{1-6}$ alkyl, phenyl or phenyl-$C_{1-6}$ alkyl, which phenyl moieties may be substituted by $C_{1-6}$ alkyl, $C_{1-6}$ alkoxy or halogen;
Ar is a group of formula (a):

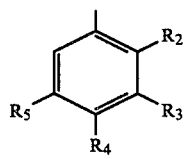

wherein either
$R_2$ is $C_{1-6}$ alkoxy and one of $R_3$, $R_4$ and $R_5$ is hydrogen and the other two are selected from hydrogen, halogen, $CF_3$, $C_{1-6}$ alkoxy, $C_{1-6}$ alkyl, $C_{1-6}$-alkylthio, $C_{2-5}$ alkanoyl, $C_{1-10}$ carboxylic acylamino, $C_{1-6}$-alkyl $S(O)n$ wherein $n$ is 0, 1 or 2, nitro or amino, aminocarbonyl or aminosulphonyl optionally substituted by one or two groups selected from $C_{1-6}$ alkyl, $C_{3-8}$ cycloalkyl, $C_{3O8}$ cycloalkyl $C_{1-4}$ alkyl or phenyl $C_{1-4}$ alkyl groups any of which phenyl moieties may be substituted by one or two groups selected from halogen, $CF_3$, $C_{1-6}$ alkyl or $C_{1-6}$ alkoxy; or $R_2$ is hydrogen and $R_3$, $R_4$ and $R_5$ are independently selected from hydrogen, $C_{1-6}$ alkyl, hydroxy, $C_{1-6}$ alkoxy, $C_{1-6}$ alkylthio or halo; or any two on adjacent carbon atoms together are $C_{1-2}$ alkylenedioxy and the third is hydrogen, $C_{1-6}$ alkyl, $C_{1-6}$ alkoxy or halo;

or Ar is a group of formula (b);

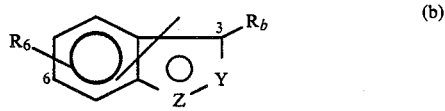

wherein
Z is $CH_2$, O, S or $NR_7$ wherein $R_7$ is hydrogen, $C_{1-6}$ alkyl, $C_{3-7}$ alkenyl-methyl, phenyl or phenyl $C_{1-4}$ alkyl either of which phenyl moieties may be substituted by one or two of halogen, $CF_3$, $C_{1-6}$ alkoxy or $C_{1-6}$ alkyl; and Y is CH or N; or Z is CH or N and Y is $NR_a$ or $CHR_a$ where $R_a$ is as defined for $R_7$ above;

$R_b$ is present when the COX linkage is attached at the phenyl ring, and is selected from hydrogen, halogen, $CF_3$, hydroxy, $C_{1-6}$ alkoxy or $C_{1-6}$ alkyl;

$R_6$ is hydrogen, halogen, $CF_3$, $C_{1-6}$ alkyl, $C_{1-6}$ alkoxy, $C_{1-6}$ alkylthio, $C_{1O7}$ acyl, $C_{1O7}$ acylamino, $C_{1-6}$ alkylsulphonylamino, N-($C_{1-6}$ alkylsulphonyl)-N-$C_{1-4}$ alkylamino, $C_{1-6}$ alkylsulphinyl, hydroxy, nitro or amino, aminocarbonyl, aminosulphonyl, aminosulphonylamino or N-(aminosulphonyl)-$C_{1-4}$ alkylamino optionally N-substituted by one or two groups selected from $C_{1-6}$ alkyl, $C_{3-8}$ cycloalkyl, $C_{3-8}$ cycloalkyl $C_{1-4}$ alkyl, phenyl or phenyl $C_{1-4}$ alkyl groups or optionally N-disubstituted by $C_{4-5}$ polymethylene.

2. A compound according to claim 1 of formula (II):

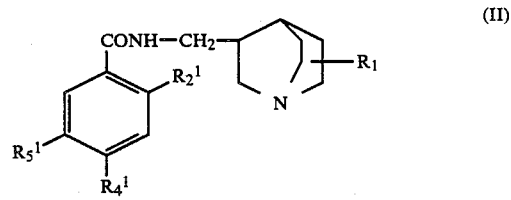

where
$R_2^1$ is a $C_{1-6}$ alkoxy;
$R_4^1$ is amino or $C_{1-7}$ alkanoylamino;
$R_5^1$ is amino or $C_{1-6}$ alkylthio;
and $R_1$ is as defined in claim 1

3. A compound according to claim 2 wherein $R_2^1$ is methoxy, $R_4^1$ is amino and $R_5^1$ is chloro or bromo.

4. A compound according to claim 2 wherein $R_1$ is hydrogen.

5. A compound according to claim 1 of formula (IV):

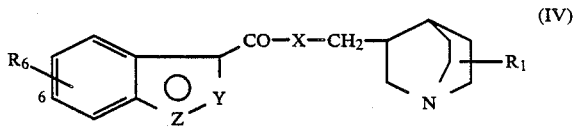

wherein $R_1$, $R_6$, X, Y and Z are as defined in claim 1.

6. A compound according to claim 5 wherein $R_6$ is hydrogen or 5-fluoro, Y is CH or N and Z is $NR_7$ wherein $R_7$ is as defined in claim 1.

7. A compound according to claim 5 wherein $R_1$ is hydrogen.

8. 4-Amino-5-chloro-2-methoxy-N-(3-quinclidinylmethyl)benzamide, or a pharmaceutically acceptable salt thereof.

9. A pharmaceutical composition for the treatment of disorders relating to impaired gastro-intestinal motility, emesis, migraine, cluster headaches or trigeminal neuralgia comprising an effective amount of a compound of formula (I) as defined in claim 1, or a pharmaceutically acceptable salt thereof, and a pharmaceutically acceptable carrier.

10. A method of treatment of disorders relating to impaired gastro-intestinal motility, emesis, migraine, cluster headaches or trigeminal neuralgia which comprises the administration of an effective amount of a compound of formula (I) as defined in claim 1, or a pharmaceutically acceptable salt thereof.

11. A pharmaceutical composition for the treatment of disorders relating to impaired gastro-intestinal motility comprising an effective amount of the compound defined in claim 8, or a pharmaceutically acceptable salt thereof, and a pharmaceutically acceptable carrier.

12. A method of treatment of disorders relating to impaired gastro-intestinal motility which comprises the administration of a the compound defined in claim 8, or a pharmaceutically acceptable salt thereof.

* * * * *